United States Patent
Perreault et al.

(10) Patent No.: US 9,694,304 B2
(45) Date of Patent: Jul. 4, 2017

(54) METHODS AND DEVICES USED FOR REDUNDANT STERILE FILTRATION

(71) Applicant: EMD Millipore Corporation, Billerica, MA (US)

(72) Inventors: Jeremy Perreault, Billerica, MA (US); Sean Foley, Billerica, MA (US); Kevin Rautio, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 14/440,370

(22) PCT Filed: Nov. 26, 2013

(86) PCT No.: PCT/US2013/071861
§ 371 (c)(1),
(2) Date: May 4, 2015

(87) PCT Pub. No.: WO2014/088882
PCT Pub. Date: Jun. 12, 2014

(65) Prior Publication Data
US 2015/0283479 A1    Oct. 8, 2015

Related U.S. Application Data

(60) Provisional application No. 61/732,551, filed on Dec. 3, 2012.

(51) Int. Cl.
*B01D 19/00* (2006.01)
*A61L 2/00* (2006.01)
(Continued)

(52) U.S. Cl.
CPC ........ *B01D 19/0031* (2013.01); *A61L 2/0017* (2013.01); *B01D 61/142* (2013.01);
(Continued)

(58) Field of Classification Search
CPC .. B01D 19/0031; B01D 53/226; B01D 63/00; B01D 2317/02; B01D 2319/02; B01D 2319/04; A61L 2/0017
See application file for complete search history.

(56) References Cited

U.S. PATENT DOCUMENTS 3,631,654 A * 1/1972 Riely ................. B01D 19/0031
210/446
4,116,646 A * 9/1978 Edwards ............ B01D 19/0031
210/436
(Continued)

FOREIGN PATENT DOCUMENTS

CN      1084426 A      3/1994
CN      1787870 A      6/2006
(Continued)

OTHER PUBLICATIONS

Chinese communication, with English translation, dated Apr. 5, 2016 in corresponding Chinese patent application No. 201380063259.4.
(Continued)

*Primary Examiner* — Jason M Greene
(74) *Attorney, Agent, or Firm* — Nields, Lemack & Frame, LLC

(57) ABSTRACT

Redundant filtration system that includes at least one barrier filter as a process filter, the barrier filter having both hydrophilic and hydrophobic paths, allowing both fluid and gas permeability. The need for vents is eliminated, as is an intermediate drain filter. The device also can be dried in series. The filtration system includes a network of conduits and receptacles, the network receiving liquid raw and/or starting material at one end, conducting it through the process stream defined thereby, and producing the desired liquid product at another end. The network is provided with one or more in-puts for introducing liquid raw material into
(Continued)

the fluid process stream, and one or more output ports for discharging fluid out of the fluid process stream. The network is preferably an essentially closed network, and also, preferably sterile and/or aseptic.

14 Claims, 9 Drawing Sheets

(51) Int. Cl.
  *B01D 61/14* (2006.01)
  *B01D 61/18* (2006.01)
  *B01D 63/08* (2006.01)

(52) U.S. Cl.
  CPC ............ *B01D 61/18* (2013.01); *B01D 63/084* (2013.01); *B01D 2313/16* (2013.01); *B01D 2313/44* (2013.01); *B01D 2315/08* (2013.01); *B01D 2317/025* (2013.01); *B01D 2317/06* (2013.01); *B01D 2325/36* (2013.01); *B01D 2325/38* (2013.01)

(56) References Cited

U.S. PATENT DOCUMENTS

| | | | | |
|---|---|---|---|---|
| 4,302,223 | A * | 11/1981 | Booth | B01D 19/0031 210/321.64 |
| 4,326,957 | A * | 4/1982 | Rosenberg | B01D 19/0031 210/436 |
| 4,459,139 | A * | 7/1984 | vonReis | B01D 19/0031 210/416.1 |
| 4,906,260 | A * | 3/1990 | Emheiser | B01D 19/0031 210/321.84 |
| 5,100,564 | A | 3/1992 | Pall et al. | |
| 5,827,429 | A | 10/1998 | Ruschke et al. | |
| 6,347,711 | B1 * | 2/2002 | Goebel | B01D 19/0031 210/436 |
| 6,623,631 | B1 | 9/2003 | Graus et al. | |
| 6,635,179 | B1 | 10/2003 | Summerton et al. | |
| 6,902,671 | B2 | 6/2005 | Cappia et al. | |
| 7,103,450 | B2 | 9/2006 | Kubiak et al. | |
| 7,534,349 | B2 | 5/2009 | Collins et al. | |
| 7,775,375 | B2 | 8/2010 | Palumbo et al. | |
| 2002/0096467 | A1 * | 7/2002 | Cappia | B01D 19/0031 210/321.6 |
| 2003/0042211 | A1 * | 3/2003 | Beplate | B01D 19/0031 210/767 |
| 2004/0182240 | A1 | 9/2004 | Bause et al. | |
| 2008/0191382 | A1 | 8/2008 | Sato et al. | |
| 2008/0197072 | A1 | 8/2008 | Ansorge et al. | |
| 2009/0182263 | A1 * | 7/2009 | Burbank | B01D 63/00 604/28 |
| 2012/0063928 | A1 * | 3/2012 | Herz | B01D 19/0031 417/313 |
| 2013/0118347 | A1 * | 5/2013 | Walter | B01D 19/0031 95/24 |
| 2013/0287678 | A1 * | 10/2013 | Okada | B01D 53/226 423/652 |

FOREIGN PATENT DOCUMENTS

| | | |
|---|---|---|
| CN | 101284195 A | 10/2008 |
| DE | 2844073 A1 | 4/1980 |
| JP | 5-161827 A | 6/1993 |
| JP | 2005-329407 A | 12/2005 |
| JP | 2009-533092 A | 9/2009 |
| WO | 02/32476 A2 | 4/2002 |
| WO | 2012/013256 A1 | 2/2012 |
| WO | WO 2012/013256 A1 * | 2/2012 ............ B01D 19/00 |

OTHER PUBLICATIONS

International Search Report/Written Opinion mailed Mar. 25, 2014 in corresponding PCT application No. PCT/US2013/071861.
International Preliminary Report on Patentability mailed Jul. 23, 2015 in corresponding PCT application No. PCT/US2013/071861.
BioProcess International, Jun. 2006, vol. 4(6), pp. S44-S47, "Preparation of Redundant, Disposable Filtration Systems", Lentine, et al.
European communication dated Aug. 19, 2016 in corresponding European patent application No. 13859871.9.
Japanese communication, with English translation, dated May 24, 2016 in corresponding Japanese patent application No. 2015-545173.

* cited by examiner

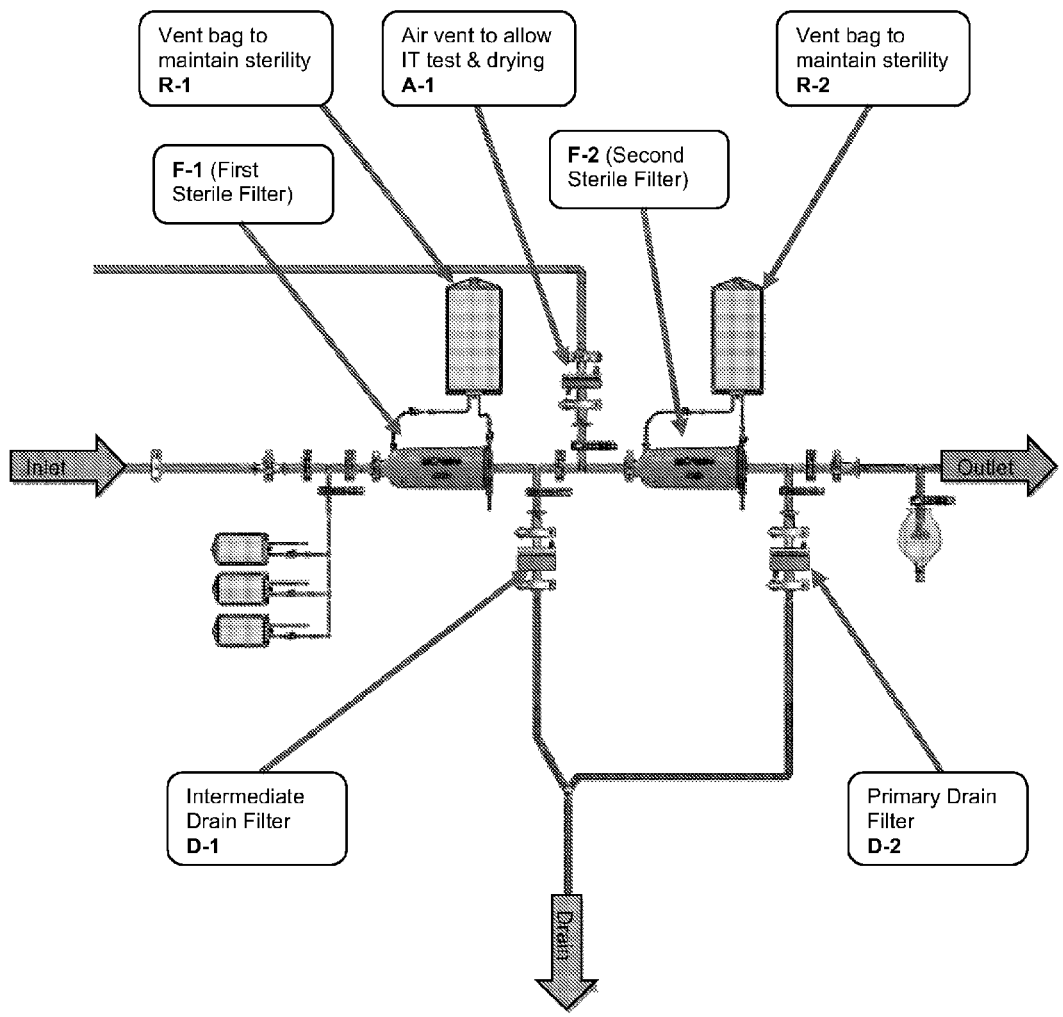
Figure 1: Component Description of current SURF system (Prior Art)

Figure 2: <u>Existing SURF operation: Flush (Prior Art)</u>
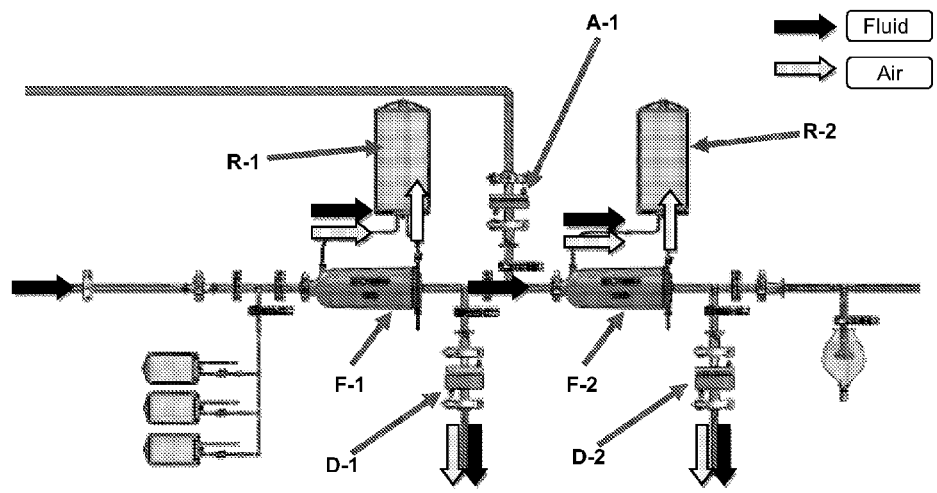
Figure 3: <u>Existing SURF operation: Integrity Test & Dry (Prior Art)</u>
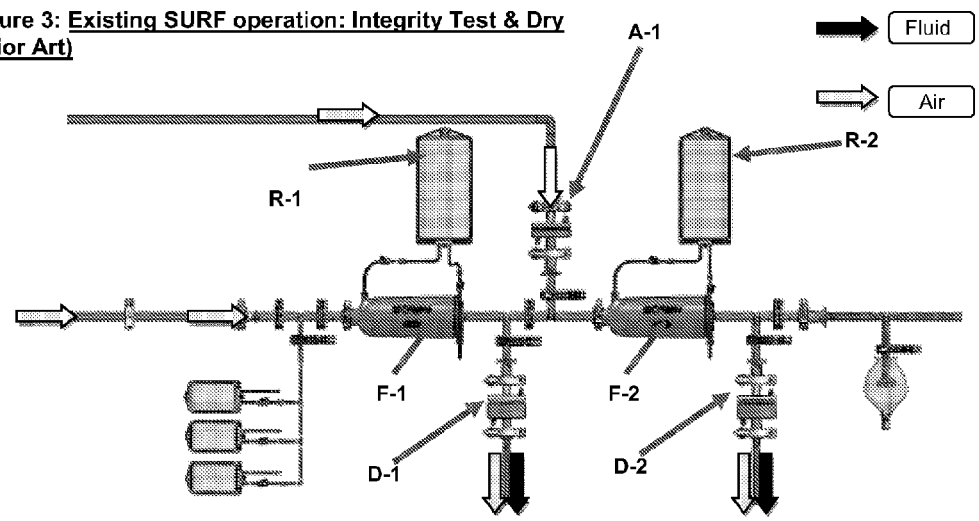

Figure 4: Barrier Filter used in F-2: Flush
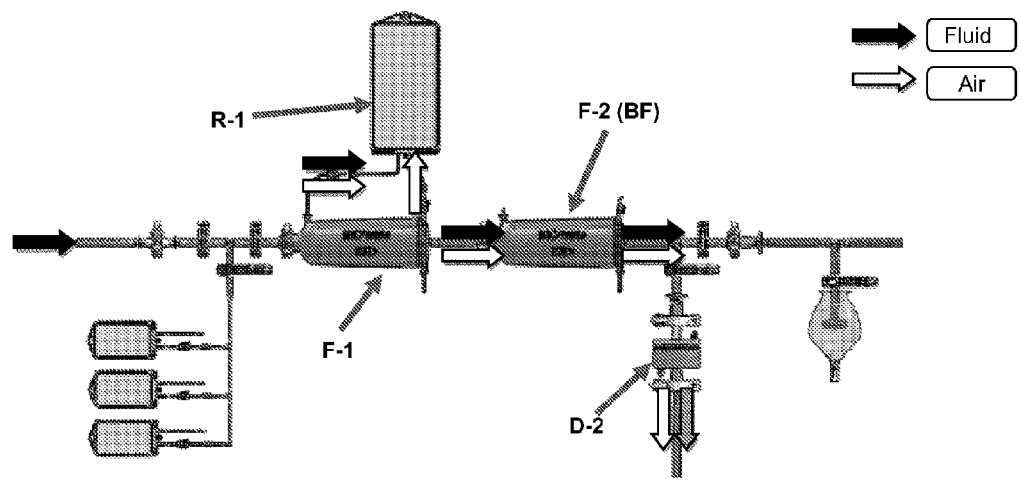
Figure 5: Barrier Filter used in F-2: Integrity Test & Dry
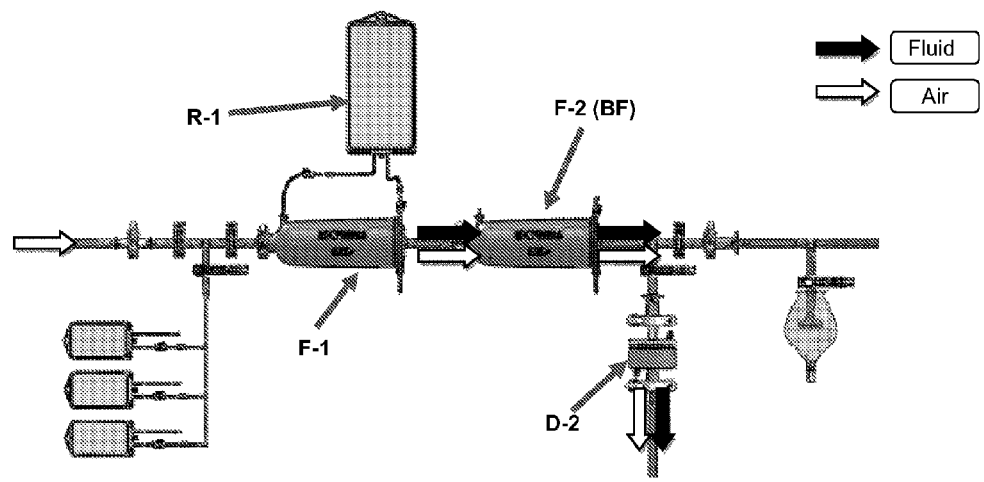

Figure 6: Barrier Filter used in F-1: Flush
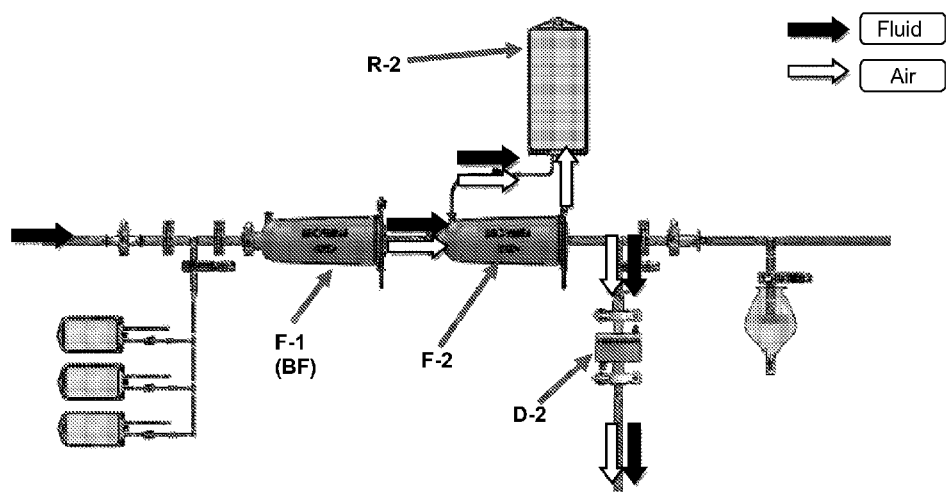
Figure 7: Barrier Filter used in F-1: Integrity Test & Dry
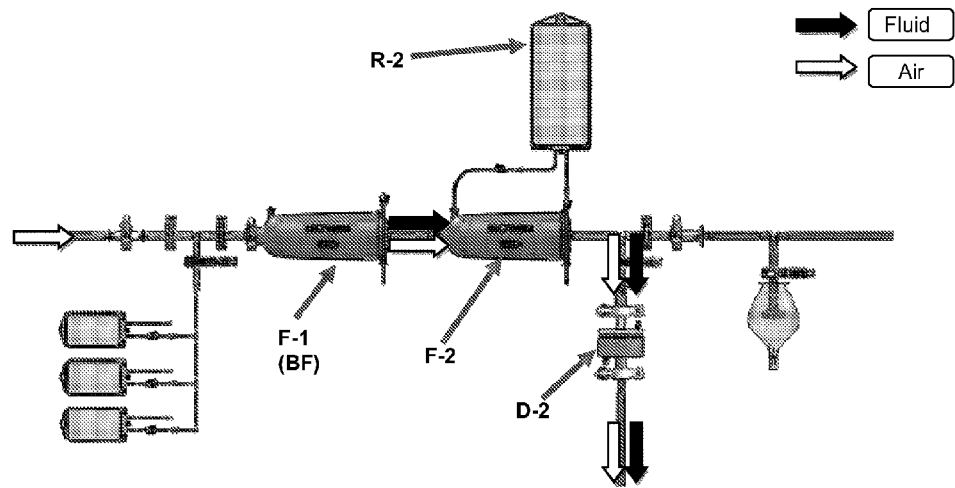

Figure 8: Barrier Filter used in F-1 & F-2: Flush
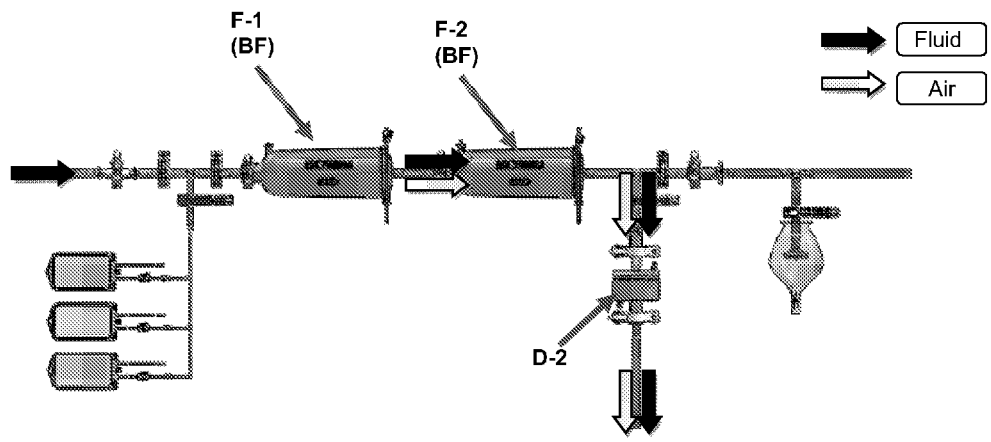
Figure 9: Barrier Filter used in F-1 & F-2: Integrity Test & Dry
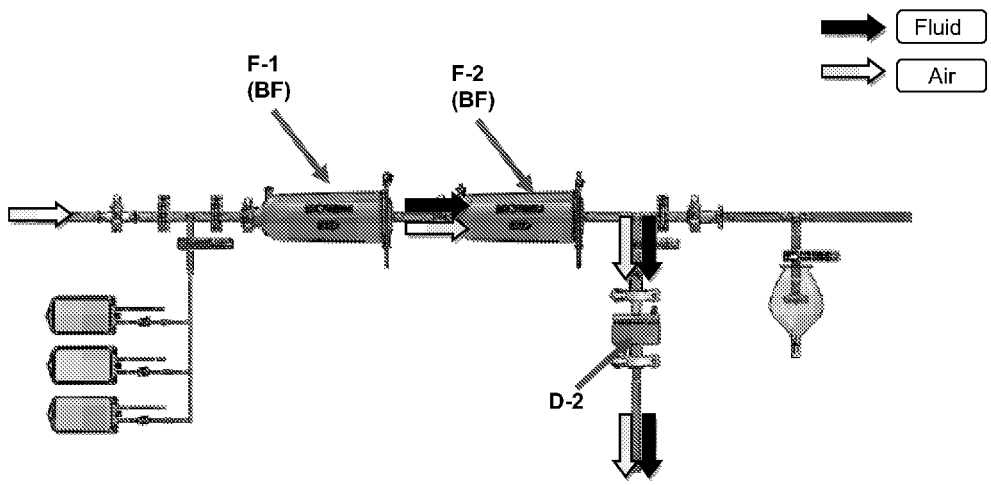

Figure 10: Device Design Utilizing Barrier Filter in F-1 Position
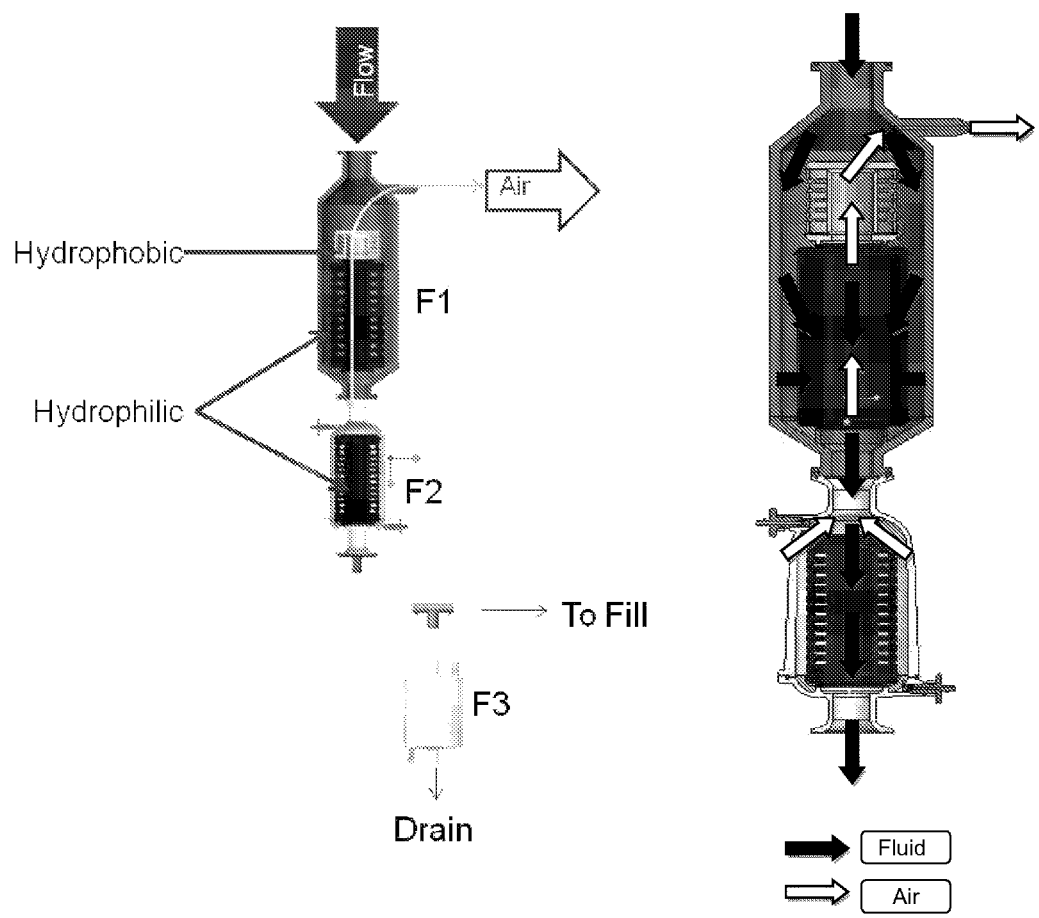

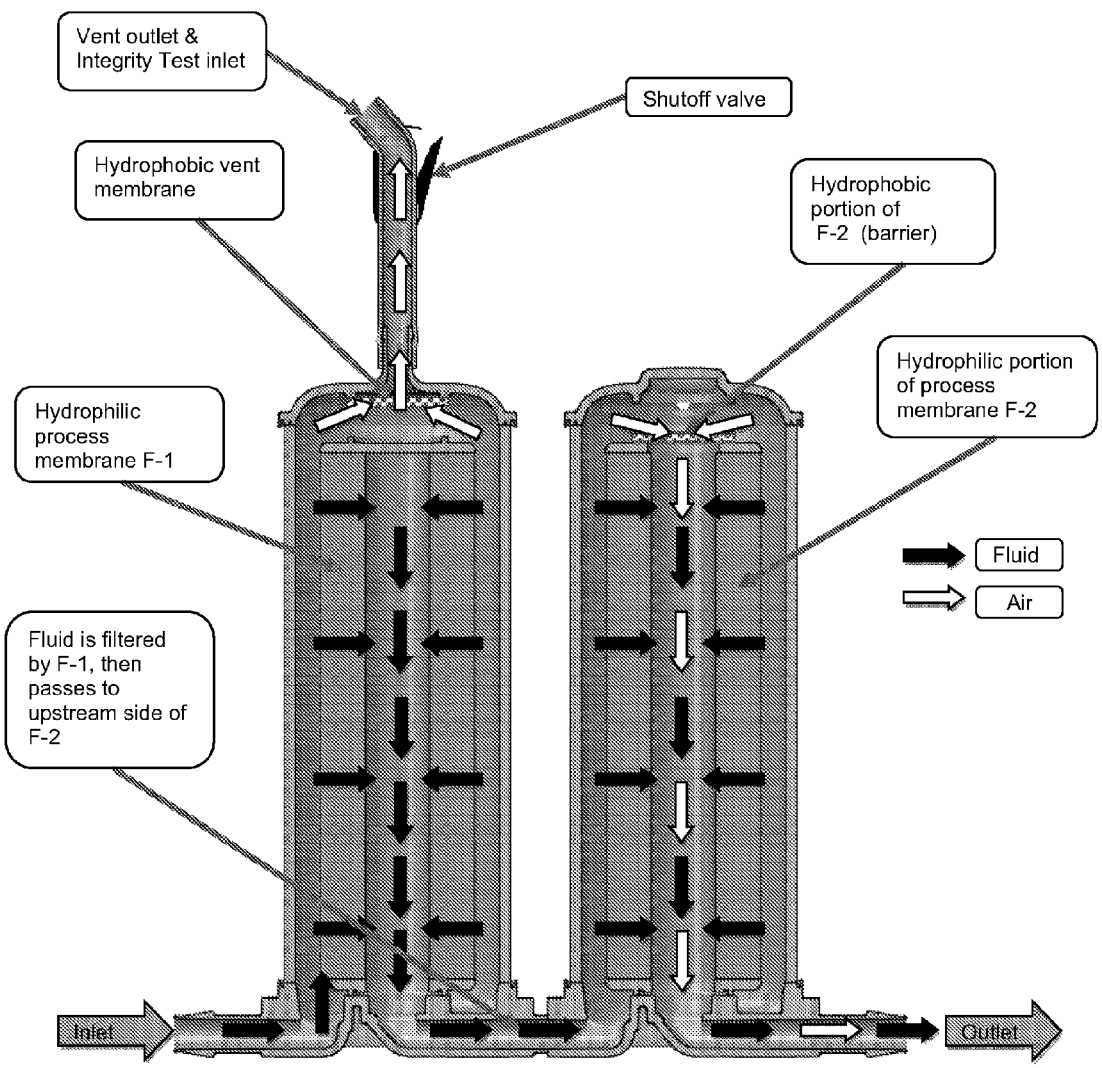
Figure 11: Device Design Utilizing Barrier Filter in F-2 Position

Figure 12: Device Design Utilizing Barrier Filter in F-1 Position
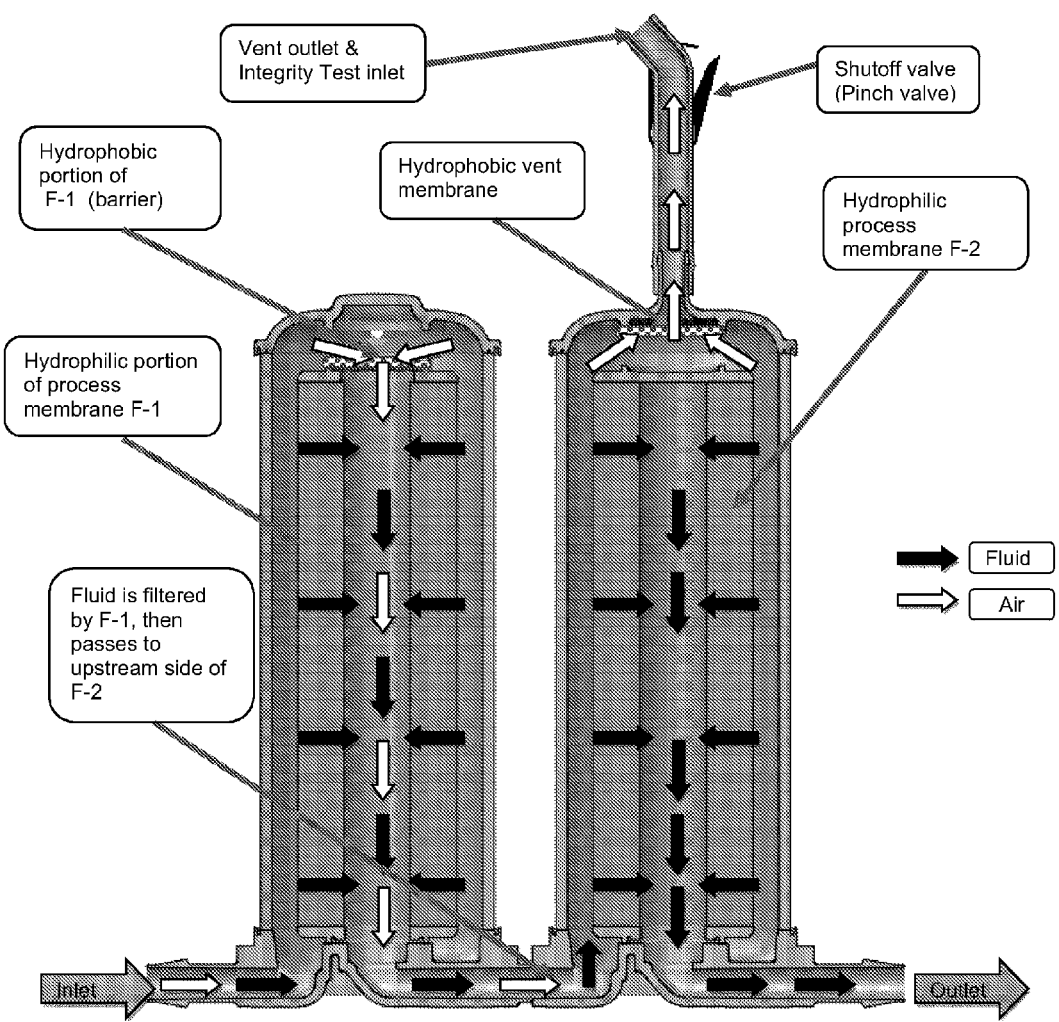

Figure 13: <u>Device Design Utilizing Typical Hydrophilic Filters in F-1 & F-2 Position</u>
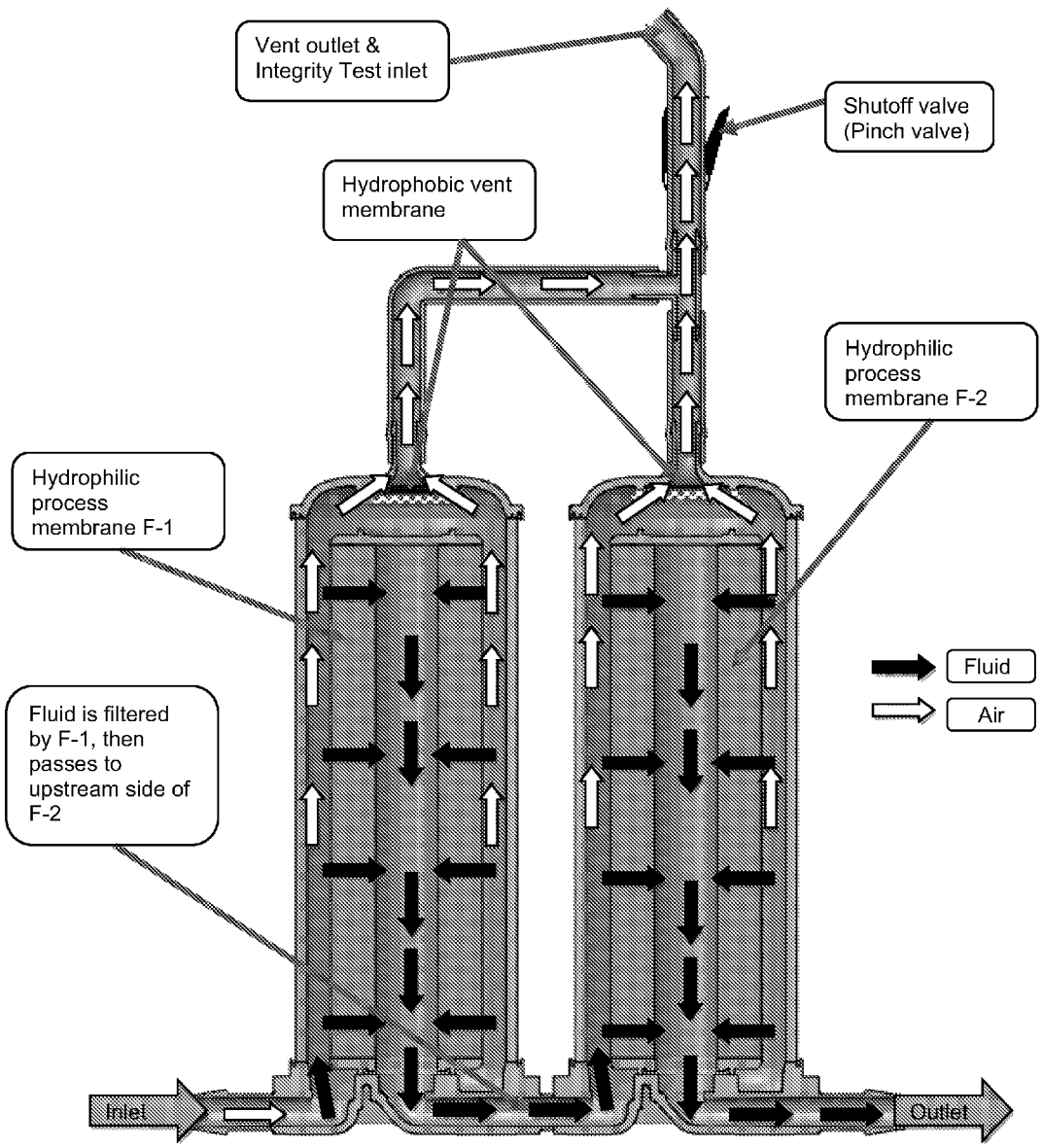

METHODS AND DEVICES USED FOR REDUNDANT STERILE FILTRATION

This application claims priority of U.S. Provisional Application Ser. No. 61/732,551 filed Dec. 3, 2012, the disclosure of which is incorporated herein by reference.

BACKGROUND

The filling operation for bulk drug substances is a critical final step that requires sterile processing to assure product quality. It is imperative that the manufacturer be able to determine that the final assembly is integral prior to quality assurance release. Indeed, as the market for biopharmaceuticals continues to grow, manufacturers must be certain to follow the strict regulatory guidelines for the production of these drugs. Because most biopharmaceuticals are administered by injection, their sterility is crucial to the safety of the patient receiving the drug therapy. Filtration is a critical quality-assurance strategy for injectable drugs. In guidelines published in 2004, the US Food and Drug Administration suggested the use of redundant sterilizing filters. This is generally defined as a type of serial filtration in which a second sterilizing-grade filter is used as a backup in the event of an integrity failure of the primary sterilizing filter. The second sterilizing-grade filter is incorporated in line, usually upstream but possibly downstream, to provide additional assurance of sterilizing filtration. This can be particularly important for batches that cannot be reworked in the event of a sterilizing filter integrity failure, resulting in complete loss of the batch often at consideration expense.

While redundant sterile filtration reduces the risk of losing a batch due to an integrity failure, it introduces considerable complication to the process. Typically the filters are flushed, integrity tested and dried before use. When configured in a redundant sterile filtration mode, any point downstream of the first filter must remain sterile. This requires the use of additional air and drain filters to allow the pre-use preparation. It also requires a significant amount of operator interaction to open and close numerous valves in the correct sequence to carry out the various flushing, testing and drying operations. This complication and chance for operator error introduces the opportunity of breaching sterility or creating some other failure type. Most significant, however, is the increase in product loss due to the increased working volume. Product cost is often in the hundreds of dollars per milliliter, so even small losses can be costly.

Where redundant filtration is employed, typically it involves using two sterilizing grade 0.2 µm hydrophilic capsule filters in series. However, this presents several issues, since hydrophilic filters will not allow air passage once wet. Venting air from the capsules requires either a separate sterile vent filter or more commonly a closed, sterile waste reservoir to vent into. Pre-use integrity testing of the capsules requires an intermediate drain filter between them to allow downstream flow. Drying the cartridges before introducing product requires exceeding the bubble point pressure of the membrane with compressed air for approximately 20 minutes. When two capsules are attached in series, it is typically difficult to execute this drying step due to the additive pressure drop across both devises and the overall working pressure rating of the housings. For this reason, the capsules are typically dried separately through the intermediate drain filter and an additional air inlet filter placed before the second sterile filter.

Given the extremely low failure rate of the existing single stage filtration system, the added complexity of redundant filtration is difficult to justify financially. However, if that complexity could be reduced or eliminated, the benefit of redundant sterile filtration could be realized.

It therefore would be desirable to provide a device and methodology that utilizes redundant filtration with ease of use and product yield comparable to single stage solutions.

SUMMARY

The problems of the prior art have been overcome by the embodiments disclosed herein, which provide a redundant filtration system that includes at least one barrier filter as a process filter, the barrier filter having both hydrophilic and hydrophobic paths, allowing both fluid and gas permeability. By substituting one or both of the sterile process filters used in a conventional single use redundant filter design with a barrier filter, the need for vents is eliminated, as is the intermediate drain filter. The device also can be dried in series.

In accordance with certain embodiments, the filtration system includes a network of conduits and receptacles, the network receiving liquid raw and/or starting material at one end, conducting it through the process stream defined thereby, and producing the desired liquid product at another end. The network is provided with one or more inputs for introducing liquid raw material into the fluid process stream, and one or more output ports for discharging fluid out of the fluid process stream. The network is preferably an essentially closed network, and also, preferably sterile and/or aseptic.

BRIEF DESCRIPTION OF THE DRAWINGS

FIG. 1 is a schematic diagram of a redundant filtration system in accordance with the prior art;

FIG. 2 is a schematic diagram of the system of FIG. 1 in a flush mode;

FIG. 3 is a schematic diagram of the system of FIG. 1 in an integrity test and dry mode;

FIG. 4 is a schematic diagram of a redundant filtration system in a flush mode in accordance with certain embodiments;

FIG. 5 is a schematic diagram of the redundant filtration system of FIG. 4 in an integrity test and dry mode;

FIG. 6 is a schematic diagram of a redundant filtration system in a flush mode in accordance with certain embodiments;

FIG. 7 is a schematic diagram of the redundant filtration system of FIG. 6 in an integrity test and dry mode;

FIG. 8 is a schematic diagram of a redundant filtration system in a flush mode in accordance with certain embodiments;

FIG. 9 is a schematic diagram of the redundant filtration system of FIG. 8 in an integrity test and dry mode;

FIG. 10 is a schematic diagram of a barrier filter in a vertical arrangement in accordance with certain embodiments;

FIG. 11 is a cross-sectional view of a filter configuration in accordance with certain embodiments;

FIG. 12 is a cross-sectional view of another filter configuration in accordance with certain embodiments; and FIG. 13 is a cross-sectional view of yet another filter configuration in accordance with certain embodiments.

DETAILED DESCRIPTION

Turning first to FIG. 1, there is shown schematically a conventional single use redundant filter design. The system includes the requisite network of conduits, including one or more inlets (e.g., for gas and water), one or more outlets (e.g., a drain and a product outlet), and appropriate valving, defining a fluid process stream designed to receive starting material at an inlet, conduct it through the process stream including a filtration train, and producing the desired product to be discharged at an outlet. The filtration train includes a first sterile process filter F-1, and a second sterile process filter F-2 in series with and downstream of the first sterile process filter F-1. An intermediate drain filter D-1 is positioned between filters F-1 and F-2, and a primary drain filter D-2 is positioned downstream of filter F-2 as shown.

It should be understood by those skilled in the art that a process filter or membrane is that employed in the system for the purpose of conducting the system's manufacturing process to yield product. The manufacturing process will either not yield the desired product or otherwise yield a markedly different product (i.e., in respect of purity, concentration, and the like) in the absence of the process filter or membrane component. The process filter or membrane component is positioned within the fluid process stream and is capable of filtering the aforementioned liquid raw material as it passes therethrough. The term "process filter" as used herein is therefore different from a drain filter, which is not used to filter product, but rather is in the network to enable integrity testing and maintain system sterility at the drain outlet.

The flushing of the system of FIG. 1 is shown schematically in FIG. 2, and the integrity test and drying operation is shown schematically in FIG. 3. An intermediate air filter A-1 is positioned between the first and second process filters, and is provided to integrity test or dry F-2, and first and second closed sterile waste reservoirs or vent bags R-1 and R-2 are provided in fluid communication with the first and second process filters, respectively, to receive the respective vented air from filters F-1 and F-2. Downstream flow during integrity testing and drying of F-1 is enabled by the use of the intermediate drain filter D-1 positioned between the process filters F-1 and F-2. Integrity testing and drying of F-2 is performed with air administered through A-1 with downstream flow of F-2 enabled by the use of the drain filter D-2.

By substituting a barrier filter for one or both of the sterile process filters F-1 and/or F-2, the need for the intermediate drain filter D-1, the intermediate air filter A-1, and the vent bag on the housing containing the barrier filter can be eliminated.

For example, in accordance with certain embodiments as shown in FIG. 4, the second, downstream process filter is a barrier filter BF. The use of a barrier filter enables the elimination of the vent bag R-2 on the second downstream filter. This is because the barrier filter contains hydrophilic and hydrophobic regions, which allows any air upstream of F-2 to pass downstream without needing to be vented.

In addition, as shown in FIG. 5, the entire system can be dried in series as a single operation, which eliminates intermediate air filter A-1 and intermediate drain filter D-1. This is possible because the barrier filter allows gas and liquid flow, which means air flow through the system can be accomplished by exceeding the bubble point of F-1 (~50 psi). This is in comparison to the current state of the art, which would require an air inlet pressure which exceeds the sum of the bubble point pressures for F-1 and F-2 (>100 psi). The pressure required to accomplish this typically exceeds the maximum working pressure rating of the intermediate components and is therefore not practical.

FIGS. 6 and 7 illustrate an embodiment where the upstream process filter is a barrier filter BF. This also enables the elimination of the intermediate air filter, the intermediate drain filter, and enables the elimination of the vent bag on the upstream filter for the same reasons as described above: a) Venting of the F-1 filter is no longer necessary since any air present will flow downstream b) F-1 and F-2 can be dried in series due to the barrier filter's ability to allow gas flow when wet. In addition, in this embodiment, pre-use integrity testing can be carried out on the downstream filter F-2 (FIG. 7), which is preferred since it is closer to the final point of use (a filling machine).

FIGS. 8 and 9 illustrate a further embodiment where both process filters in series are barrier filters BF. Since barrier filters can pass air downstream, the filter housing does not require vents. This, combined with the ease with which they can be dried, results in the elimination of all venting operations and necessary vent bags along with the intermediate drain and air filters. As a result, minimal operator manipulation is required other than redirection of flow from the drain to the filling machine upon completion of the drying operation. However, pre-use integrity testing of the filters is not possible in this embodiment, since barrier filters only can be tested after wetting with isopropyl alcohol, which is not practical since verification of the complete removal of the alcohol would be required prior to introducing the product into the system. However, post-use testing can be readily performed.

FIG. 10 illustrates a further embodiment that simplifies the overall system with a unique vertical configuration of the filtration stages with F-1 configured as a barrier filter and F-2 a typical sterilizing grade hydrophilic filter. This is functionally equivalent to the embodiment shown in FIGS. 6 & 7 with the exception of the vent path for F-2. When positioned vertically and designed to allow proper flow, the air entrapped within process filter F-2 is allowed to rise through the housing and backflow through the hydrophobic portion of F-1. This is unique in that the air is passed back to the upstream side of filter F-1, which is considered to be the non-sterile side of the device. This means the air vent valve and associated means of managing the vented air/liquid does not need to be verified for integrity; this places the vent upstream from the sterilizing membranes, which means it can be opened to the surrounding environment without breaching sterility. Venting to the upstream side of the barrier filter F-1 of FIG. 10 allows for the elimination of the vent bag shown on F-2 in FIGS. 6 and 7.

In accordance with certain embodiments, a hydrophobic membrane may be integrated into the vent (FIG. 11) such that it can vent directly to atmosphere without requiring a vent bag. After a hydrophilic membrane is wet, it will not allow air to pass through. When first introducing liquid to the system, or if a user chooses to introduce product after flushing with water but not drying, it is necessary to vent the air from the system. Historically this has been accomplished with vent ports/valves which allow the air to escape the filter housing to the environment. In this application that is considered unacceptable because opening the vent to atmosphere could breach sterility, and the final fill/filter application is conducted in a highly controlled area and allowing fluid to escape the filter would be considered a contamination of the environment. If a hydrophobic membrane is placed in line with the vent, it will maintain sterility and prevent liquid from escaping.

As compared to the current state of the art shown in FIG. 1, the configuration shown in FIG. 10 eliminates the need, during wetting, to isolate the air inlet line between F-1 and F-2, to remove the clamp normally present between F-1 and F-2 and isolate F-3 from F-2, to fill F-2 while venting out the top of F-2 and to close the vent. This is enabled by the elimination of A-1 and D-1, along with configuring F-1 and F-2 as a single housing which eliminates the need for all but a single vent. Thus, wetting simply involves connecting a water supply to F-1 and fill the housing, venting out the top, closing the vent, and unclamping F-3 and flowing to drain.

The configuration shown in FIG. 10 also eliminates the need, during draining, to connect an air supply to the vent filter between F-1 and F-2 to drain F-2 since the air upstream of F-1 can freely pass through the barrier filter to F-2. Thus, draining simply requires connecting an air supply to F-1 upstream of F-2 to drain F-1.

The configuration shown in FIG. 10 also eliminates the need, during integrity testing, to isolate F-1 from F-2 and the vent filter, to attach an integrity tester to the vent filter and test F-2, and to isolate F-2 from F-1 and the vent filter since the barrier filter in F-1 is transparent to a typical bubble point or diffusion integrity tester. Thus, integrity testing simply requires attaching the integrity tester to F-1 and testing F-2.

The configuration shown in FIG. 10 also eliminates the need, during drying, to isolate F-1 from F-2 and the vent filter, and to attach an air supply to the vent filter and exhaust F-2 through F-3. Thus, drying simply requires attaching an air supply to F-1 and exhausting through the vent filter (F-3).

FIG. 11 shows a configuration wherein two devices are combined into one, and an integrated hydrophobic vent is added to the top of the filter chamber of F-1 to eliminate the vent bag. The fluid enters the inlet and flows through a hydrophilic process membrane F-1 in the first stage, then passes to the upstream side of the second stage where it is filtered through the hydrophilic portion of the process membrane F-2 (the barrier filter). The first chamber or stage (in the direction of flow) includes a hydrophobic vent membrane. The second chamber or stage includes a hydrophobic portion of the membrane as shown. The top of the barrier filter is open (the end cap has hole in center) with a piece of hydrophobic membrane placed over it. As flow is introduced and fluid passes through the hydrophilic portion, there is a pressure drop across the filter. This likewise creates a pressure differential across the hydrophobic layer of membrane since the downstream side of the membrane is shared with the downstream side of the hydrophilic portion of the filter. This differential pressure causes the air at the top of the chamber to flow through to the downstream side. The liquid flow velocity in these applications is sufficient to create turbulence and carry air bubbles further downstream which removes the air in the downstream core of the filter. This continues until the fluid height in the F-2 chamber has risen to cover the hydrophobic membrane. Since aqueous solutions cannot cross the hydrophobic membrane layer, this effectively closes this path within F-2 and the product to be filtered passes through the hydrophilic regions. This configuration can be used with the system of FIG. 4 and would follow a similar method of use. Combining the individual filters into a single device reduces the size and complexity of the system to both manufacture and operate. It allows the elimination of R-1 since contamination cannot pass the sterilizing grade hydrophobic membrane into the system nor can product escape the system and contaminate the surrounding environment.

FIG. 12 shows a configuration wherein two devices are combined into one and an integrated hydrophobic vent with a shutoff valve is added to the top of the filter chamber of F-2 to eliminate the vent bag. The fluid enters the inlet and flows through a hydrophilic portion of the process membrane F-1 in the first stage, then passes to the upstream side of the second stage where it is filtered through the hydrophilic process membrane F-2. The first chamber or stage (in the direction of flow) includes a hydrophobic portion of the membrane as shown. The second chamber or stage includes a hydrophobic vent membrane. This configuration can be used with the system of FIG. 6. This allows the elimination of R-2 since contamination cannot pass the sterilizing grade hydrophobic membrane into the system nor can product escape the system and contaminate the surrounding environment.

FIG. 13 shows a configuration with two typical hydrophilic filters and a hydrophobic vent at the top of both filter chambers. These vents are then connected together to form a single vent outlet for ease of use. The fluid enters the inlet and flows through a hydrophilic process membrane F-1 in the first stage, then passes to the upstream side of the second stage where it is filtered through the hydrophilic process membrane F-2. Each chamber or stage includes a hydrophobic vent membrane. This allows the elimination of R-1 and R-2 since contamination cannot pass the sterilizing grade hydrophobic membrane into the system nor can product escape the system and contaminate the surrounding environment. Additionally, an air bypass is created by connecting the vents of F-1 and F-2. This allows F-1 and F-2 to by dried in series which is not practical in the conventional embodiment shown in FIG. 1 due to the additive pressures necessary to exceed the bubble point of both filters.

Each of the chambers or stages in the embodiments of FIGS. 10-13 can be a perforated outer sleeve, have folds of membrane within, and a perforated central core. The flow path is from the outside to the inner perforated core and then out through the center of the device. Thus, the outlet of F-1 (center of filter) flows into the inlet side of the F-2 chamber. It then flows through the membrane of F-2, down the center core of F-2, and to the outlet of the device. As fluid is introduced into the system, the internal pressure rises above atmospheric. The wetted hydrophilic membrane will not allow air to pass through it. Any air within the filter chamber then rises to the top and passes through the hydrophobic membrane which will not allow aqueous fluid to pass. It is then vented to atmosphere.

These device housings could be constructed by any of the typical processes known to those skilled in the art. For example, more than one component joined by fasteners and elastomeric seals, parent material welding or bonding, or use of an intermediate material to adhere the components together can be used. Suitable components included molded thermoplastic, but could readily be made by machining or any other form of production suitable for the material chosen. The typical materials of construction would be anything which is currently accepted for use in the pharmaceutical industry, including polypropylene, polyethylene, PVDF, polysulfone, polycarbonate, or PTFE. Additionally, stainless steel also can be used, which is accepted as an industry standard. The filtration devices shown within these housings could be produced by any of the typical methods used in production today. This includes pleated membranes assembled with thermoplastic endcaps, thermoplastic disks with attached membrane, spirals or any other method of production. The filtration devices and housing could be integrated by any of the assembly techniques noted as possible for assembling the housing itself.

Suitable barrier filters for a process filters in the embodiments disclosed herein are disclosed in U.S. Pat. No. 6,902,671, the disclosure of which is hereby incorporated by reference. In accordance with certain embodiments, the barrier filter comprises a filter comprising, within a common enclosure, one or several filter membranes having singularly or collectively a mixture or hydrophobic and hydrophilic regions, the common enclosure having a fluid inlet, a fluid outlet, and a fluid path therebetween, all filter membranes being located within the fluid path. For example, the filter can be configured as a so-called process scale cartridge or capsule filter device provided with wrapped, wound, or stacked hydrophobic and hydrophilic membrane material. The use of hydrophilic and hydrophobic membrane material within a single filter unit effectively enables a balanced combination of good gas and liquid filtration functionality.

The common enclosure of the filter can be structured in various formats and dimensions, employing a variety of materials. Common formats include, but are not limited to, box-like cassettes, disks, and long or squat cylinders. It is preferred that the common enclosure be structured such that, but for the enclosure's inlet and outlet, the internal volume contained thereby is essentially "closed". The enclosure's inlet and outlet, in combination with the filter's internal structure, will determine the process stream through which fluid is conducted through the filter. The filter membrane component of the filters can be positioned within the process stream in several arrangements. For example, the membrane components can be positioned tangentially or orthogonally along the process stream. The membrane component may be either a singular unit (e.g., a pleated tubular membrane) or a plurality of individual units (e.g., a stack of individual membrane disks).

The barrier filter can be constructed using any of several commercially-available or otherwise publicly-accessible membranes or membrane technologies. A preferred membrane material is hydrophobic polyvinylidene fluoride (PVDF) membrane. Such inherently hydrophobic membrane can be rendered hydrophilic by applying or otherwise treating the surface thereof with a hydrophilic monomer, oligomer, or polymer. Chemical surface treatment, such as coating or grafting, can be used. Suitable processes for rendering membranes hydrophilic are known. It is preferred that the "hydrophilization" process employed should simply render the initially cast membrane sufficiently hydrophilic for use in aqueous filtration, without changing, modifying, or otherwise altering the pore size, membrane structure, hydrophobic bubble point, or microbial retention characteristics of the base membrane.

Other materials useful as membranes include, but are not limited to, nylons and other polyamides such as Nylon 6 and Nylon 66, PTFE, polysulphones, polyethersulphones, polyarylsulphones, nitrocellulose, cellulose acetate, polyolefins (such as ultrahigh molecular weight polyethylene, low density polyethylene, and polypropylene), thermoplastic fluorinated polymers (such as poly(TFE-co-PFAVE)), polycarbonates, and the like.

Suitable base membranes include DURAPORE® PVDF membrane and Express PES membrane, both commercially available from EMD Millipore Corporation of Bedford, Mass.

When employing naturally hydrophobic membrane, such as PTFE or PVDF, it is preferred, especially in the pleated format, that only portions or regions of the membrane be rendered hydrophilic. This may be accomplished, for example, by covering in the course of hydrophilization those areas or regions which should remain hydrophobic with a removable mask made of, for example, MYLAR® films, glass, metal plates, or other sufficiently impermeable materials.

The utilization of the differentiated membrane regions in a common barrier filter device, among other things, ensure that both filter membranes can be operated within their appropriate pressure ranges, in particular, there will be little or no chance for the sterilizing grade phobic membrane to be pressurized beyond its intrusion pressure, risking breach thereof, as the hydrophilic membrane, though wet, provides a highly permeable path for the release of excess gas. In essence, the permeability of the hydrophilic membrane provides an upper limit for the amount of gaseous pressure that can accumulate within the barrier filter.

In accordance with certain embodiments, the barrier filter can comprise a plurality of hydrophilic membrane discs stacked together with a hydrophobic membrane disc inserted between two hydrophilic membrane discs. In accordance with certain embodiments, the hydrophobic and hydrophilic membrane discs are Durapore® membrane discs, which are PVDF-based membranes available from EMD Millipore Corporation. In accordance with certain embodiments, the hydrophilic membranes and the hydrophobic membranes are arranged in a stack in a uniformly alternating pattern.

In accordance with certain embodiments, the barrier filter can be provided in a well-known filter cartridge format, e.g., a single tubular pleated membrane sheet having differentiated regions of hydrophobicity and hydrophilicity. The single tubular pleated sheet is maintained in its relatively fixed tubular conformation within the filter cartridge by use of external and internal supports, such supports are made of rigid material and provided with uniformly dispersed holes to allow the inward flow of fluid from regions peripheral to the membrane, then through the membrane into the filter cartridge core, and then outwardly therefrom. The filter cartridge can be provided with an external sleeve equipped with and inlet and outlet. The inlet leads into the said peripheral regions, and the core leads into the outlet.

The pleated sheet configuration can be a single membrane sheet, or a plurality of pleated membrane sheets, each sheet being individually either hydrophobic or hydrophilic. Each sheet can individually form a pleated tube, with the tubes being co-axially inserted one into the other, or each sheet can define one arcuate side of a single pleated tube.

In accordance with certain embodiments, the common enclosure is a substantially cylindrical tube and the membranes are circular, and said hydrophilic membranes and said hydrophobic membranes are arranged in said stack in a uniformly alternating pattern.

EXAMPLE 1

Order of Operation for Embodiment Shown in FIGS. 1, 2 & 3:

Flushing: Close valves to isolate F-2, A-1, D-1, D-2 & OUTLET. Connect INLET to water suitable for flushing and begin flow. Open vent valves on F-1 and allow entrapped air to flow into R-1. Close vent valves on F-1 when air has been evacuated. Open valve isolating F-2 along with vent valves on F-2 and allow entrapped air to flow into R-2. Close vent valves on F-2 when air has been evacuated. Open valve isolating D-2 and flush the system as desired.

Integrity Testing: After completing the flushing operation, close the valve isolating F-1 from F-2. Open the valve isolating A-1 and follow standard procedures for integrity testing F-2. F-1 is tested by opening the valve isolating D-1 and integrity testing through the INLET port of the system.

Drying: After completing the integrity test operation, F-1 and F-2 can be dried independently by air pressure above the membrane bubble point to INLET for F-1 and A-1 for F-2.

Filtration: Close valves to isolate F-2, A-1, D-1, D-2 & OUTLET. Connect INLET to product which is to be filtered and begin flow. Open vent valves on F-1 and allow entrapped air to flow into R-1. Close vent valves on F-1 when air has been evacuated. Open valve isolating F-2 along with vent valves on F-2 and allow entrapped air to flow into R-2. Close vent valves on F-2 when air has been evacuated. Open valve isolating OUTLET and conduct filtration operation.

EXAMPLE 2

Order of Operation for Embodiment Shown in FIGS. 4&5:
Flushing: Close valves to isolate F-2, D-2 & OUTLET. Connect INLET to water suitable for flushing and begin flow. Open vent valves on F-1 and allow entrapped air to flow into R-1. Close vent valves on F-1 when air has been evacuated. Open valve isolating F-2. Open valve isolating D-2 and flush the system as desired.
Integrity Testing: After completing the flushing operation, F-1 is integrity tested through the INLET port following standard procedures. F-2 is not pre-use tested.
Drying: After completing the integrity test operation, F-1 and F-2 can be dried simultaneously by applying air pressure to the INLET port such that it exceeds the bubble point of F-1.
Filtration: Close valves to isolate F-2, D-2 & OUTLET. Connect INLET to product which is to be filtered and begin flow. Open vent valves on F-1 and allow entrapped air to flow into R-1. Close vent valves on F-1 when air has been evacuated. Open valve isolating F-2. Open valve isolating OUTLET and conduct filtration operation.

EXAMPLE 3

Order of Operation for Embodiment Shown in FIGS. 6&7:
Flushing: Close valves to isolate D-2 & OUTLET. Connect INLET to water suitable for flushing and begin flow. Open vent valves on F-2 and allow entrapped air to flow into R-2. Close vent valves on F-2 when air has been evacuated. Open valve isolating D-2 and flush the system as desired.
Integrity Testing: After completing the flushing operation, F-2 is integrity tested through the INLET port following standard procedures. F-1 is not pre-use tested.
Drying: After completing the integrity test operation, F-1 and F-2 can be dried simultaneously by applying air pressure to the INLET port such that it exceeds the bubble point of F-2.
Filtration: Close valves to isolate D-2 & OUTLET. Connect INLET to product which is to be filtered and begin flow. Open vent valves on F-2 and allow entrapped air to flow into R-2. Close vent valves on F-2 when air has been evacuated. Open valve isolating OUTLET and conduct filtration operation.

EXAMPLE 4

Order of Operation for Embodiment Shown in FIGS. 8&9:
Flushing: Close valves to isolate D-2 & OUTLET. Connect INLET to water suitable for flushing and begin flow. Open valve isolating D-2 and flush the system as desired.
Integrity Testing: pre-use testing is not conducted with this configuration.
Drying: After completing the integrity test operation, F-1 and F-2 can be dried simultaneously by applying air pressure to the INLET port.
Filtration: Close valves to isolate D-2 & OUTLET. Connect INLET to product which is to be filtered and begin flow. Open valve isolating OUTLET and conduct filtration operation.

What is claimed is:
1. A filtration system in a manufacturing process to yield product, the filtration system comprising:
a network defining a fluid process stream, said network having one or more inputs for introducing fluid into said process stream, and one or more outlets for discharging fluid from said process stream;
a first process filter within said fluid process stream;
a second process filter within said process stream, said second process filter being positioned in series with said first process filter and downstream thereof;
wherein at least one of said first process filter and said second process filter is a barrier filter comprising, within a common enclosure, at least one hydrophilic filter membrane and at least one hydrophobic filter member and wherein the first and second process filters filter the fluid in the process stream that yields said product.
2. The filtration system of claim 1, wherein said barrier filter comprises a plurality of hydrophilic membranes and a plurality of hydrophobic membranes, and wherein said hydrophilic membranes are interspersed between said hydrophobic membranes.
3. The filtration system of claim 1, wherein said first process filter is said barrier filter.
4. The filtration system of claim 1, wherein said second process filter is said barrier filter.
5. The filtration system of claim 1, wherein both said first and said second process filters are barrier filters.
6. The filtration system of claim 1, wherein said fluid process stream is devoid of an air filter between said first and second process filters.
7. The filtration system of claim 1, wherein said fluid process stream is devoid of a drain filter between said first and second process filters.
8. A filtration train for a process stream for filtering fluid, said process stream having an inlet and an outlet for discharging a desired product from said process stream resulting from said filtration train, said filtration train being in fluid communication with said inlet and said outlet; said filtration train comprising a first process filter and a second process filter positioned in series with said first process filter and downstream thereof; wherein at least one of said first process filter and said second process filter is a barrier filter comprising, within a common enclosure, at least one hydrophilic filter membrane and at least one hydrophobic filter member, and wherein the first and second process filters filter the fluid in the process stream that yields said desired product.
9. The filtration train of claim 8, wherein said barrier filter comprises a plurality of hydrophilic membranes and a plurality of hydrophobic membranes, and wherein said hydrophilic membranes are interspersed between said hydrophobic membranes.
10. The filtration train of claim 8, wherein said first process filter is said barrier filter.
11. The filtration train of claim 8, wherein said second process filter is said barrier filter.
12. The filtration train of claim 8, wherein both said first and said second process filters are barrier filters.
13. The filtration train of claim 8, wherein said fluid process stream is devoid of an air filter between said first and second process filters.
14. The filtration train of claim 8, wherein said fluid process stream is devoid of a drain filter between said first and second process filters.

* * * * *